(12) United States Patent
Geiger et al.

(10) Patent No.: US 9,702,820 B2
(45) Date of Patent: Jul. 11, 2017

(54) IMAGING BY ATTENUATED TOTAL REFLECTANCE (ATR)

(71) Applicant: SIEMENS AKTIENGESELLSCHAFT, München (DE)

(72) Inventors: Florian Benedikt Geiger, Munich (DE); Martin Kördel, Munich (DE); Anton Schick, Velden (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 0 days.

(21) Appl. No.: 14/899,092

(22) PCT Filed: Mar. 5, 2014

(86) PCT No.: PCT/EP2014/054211
§ 371 (c)(1),
(2) Date: Dec. 16, 2015

(87) PCT Pub. No.: WO2014/202240
PCT Pub. Date: Dec. 24, 2014

(65) Prior Publication Data
US 2016/0139047 A1 May 19, 2016

(30) Foreign Application Priority Data

Jun. 21, 2013 (DE) .......... 10 2013 211 814

(51) Int. Cl.
| | |
|---|---|
| *G01N 21/55* | (2014.01) |
| *G01N 21/552* | (2014.01) |
| *G01N 21/25* | (2006.01) |
| *G01N 21/3563* | (2014.01) |
| *G01N 21/3577* | (2014.01) |
| *G01N 21/27* | (2006.01) |
| *A61B 5/00* | (2006.01) |

(52) U.S. Cl.
CPC ......... *G01N 21/552* (2013.01); *A61B 5/0075* (2013.01); *A61B 5/0086* (2013.01);
(Continued)

(58) Field of Classification Search
CPC ....................... G01N 21/552–21/554
See application file for complete search history.

(56) References Cited

U.S. PATENT DOCUMENTS 5,633,724 A * 5/1997 King .................... G01N 21/552
356/136
6,128,091 A * 10/2000 Uchida ................ G01N 21/552
250/339.11
(Continued)

FOREIGN PATENT DOCUMENTS

| | | |
|---|---|---|
| DE | 100 28 653 A1 | 12/2001 |
| DE | 698 03 343 T2 | 8/2002 |

(Continued)

OTHER PUBLICATIONS

International Search Report for PCT/EP2014/054211 mailed May 9, 2014.
(Continued)

*Primary Examiner* — Casey Bryant
(74) *Attorney, Agent, or Firm* — Slayden Grubert Beard PLLC

(57) ABSTRACT

An arrangement for attenuated total reflectance (ATR) infrared spectroscopy uses a reflection matrix for location-resolved spectroscopy of aqueous and/or powdery samples with a high signal-to-noise ratio and without previous complex preparation of the samples. The method of using the reflection matrix produces imaging of the sample with a high signal strength.

14 Claims, 3 Drawing Sheets

(52) U.S. Cl.
CPC ......... *G01N 21/253* (2013.01); *G01N 21/255* (2013.01); *G01N 21/27* (2013.01); *G01N 21/3563* (2013.01); *G01N 21/3577* (2013.01); *A61B 5/4244* (2013.01); *A61B 5/6879* (2013.01); *A61B 2505/05* (2013.01); *A61B 2562/146* (2013.01); *G01N 2201/061* (2013.01); *G01N 2201/0636* (2013.01)

(56) References Cited

U.S. PATENT DOCUMENTS

| | | | |
|---|---|---|---|
| 7,200,311 B1 * | 4/2007 | Han | B82Y 20/00 385/129 |
| 8,452,356 B2 | 5/2013 | Vestel et al. | 600/310 |

FOREIGN PATENT DOCUMENTS

| | | | |
|---|---|---|---|
| DE | 10 2013 211 814.7 | 6/2013 | |
| EP | 0 516 481 A2 | 12/1992 | |
| EP | 0 899 557 A2 | 3/1999 | |
| EP | 1 785 089 A1 | 5/2007 | |
| JP | 2001311685 A | 11/2001 | ............. G01N 21/27 |
| JP | 3399804 B2 | 4/2003 | ............. G01N 21/27 |
| JP | 2011519635 A | 7/2011 | ......... A61B 56/1459 |
| WO | PCT/EP2014/054211 | 3/2014 | |

OTHER PUBLICATIONS

Korean Office Action, Application No. 2017004049348, 6 pages, Jan. 17, 2017.

* cited by examiner

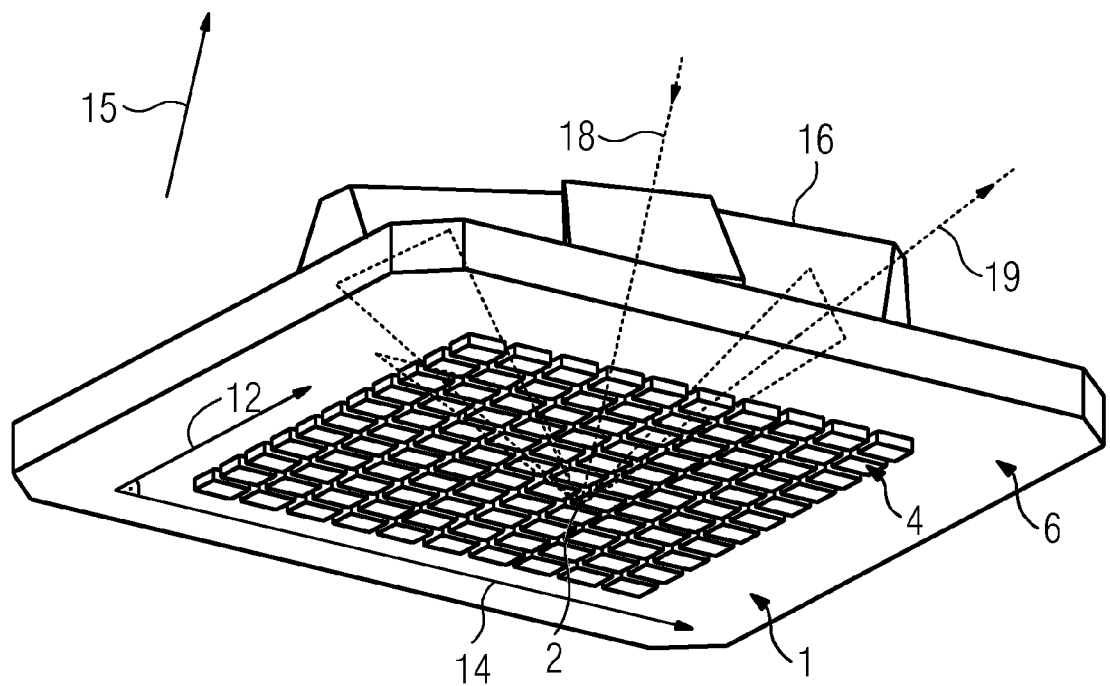

IMAGING BY ATTENUATED TOTAL REFLECTANCE (ATR)

CROSS REFERENCE TO RELATED APPLICATIONS

This application is the U.S. national stage of International Application No. PCT/EP2014/054211, filed Mar. 5, 2014 and claims the benefit thereof. The International Application claims the benefit of German Application No. 102013211814.7 filed on Jun. 21, 2013, both applications are incorporated by reference herein in their entirety.

BACKGROUND

Described below is an arrangement for infrared spectroscopy in attenuated total reflection (ATR infrared spectroscopy).

In infrared spectroscopy, a molecular spectrum of a sample to be spectroscopically analyzed is obtained by using light whose wavelength range lies in the infrared. In inorganic and organic substances, the infrared radiation is typically absorbed by excitation of mechanical oscillations of one or more molecules. Excitation of rotational levels is also possible in the case of relatively small molecules. Since the oscillation or rotation energies as quantum-mechanical eigenstates are characteristic of a molecule, the molecule and its bonds can be deduced from the absorption spectrum. Infrared spectroscopy therefore allows quantitative structural clarification of substances, the identification of which is carried out with the aid of a reference spectrum.

One particular version of infrared spectroscopy is infrared spectroscopy in attenuated total reflection (ATR infrared spectroscopy). In this case, according to the related art, the infrared radiation is guided by total reflection in a reflection element. If such total reflection takes place at an interface between a sample and a reflection element, then the infrared light enters the sample exponentially at the position of the total reflection. This entering evanescent wave interacts with the sample, so that frequency ranges characteristic of the sample are absorbed. The absorbed frequency ranges are therefore then absent in the spectrum of the totally reflected light beam. Advantageously, substances or samples which are opaque for the infrared radiation used, and for which a transmission spectrum cannot therefore be obtained, can also be spectroscopically analyzed in ATR infrared spectroscopy. furthermore, ATR infrared spectroscopy is also suitable for liquid and/or powdered samples. For many applications, besides the spectral information, local resolution, i.e. imaging of the sample, is also necessary in ATR infrared spectroscopy. According to the related art, however, such imaging is affected by strong noise. Particularly for applications of ATR infrared spectroscopy in surgery, however, a high signal strength and therefore a highly sharp differentiation of healthy and diseased tissue is desirable. Another disadvantage of known ATR infrared spectroscopy when used in surgery is that the samples are always surrounded by liquids, in particular by water and/or blood. The surrounding water, however, leads to strong absorption in the spectral range of from about 4 µm to 10 µm, which is superimposed on the actual measurement signal of the tissue.

SUMMARY

An arrangement for ATR infrared spectroscopy allows position-resolved measurement of aqueous or powdered samples with strong signals.

The arrangement for infrared spectroscopy in attenuated total reflection has a light source for emitting light, in particular infrared light, beam shaping components, and a detector for detecting an image of a sample to be spectroscopically analyzed. The arrangement also includes a reflection matrix which has a multiplicity of reflection elements that are configured in order to guide a light beam by total internal reflection. The reflection elements are arranged regularly in two mutually perpendicular directions of a surface, so that they form a matrix. In particular, the surface may be curved. In this way, the reflection elements are offset relative to one another in a direction perpendicular to the two mutually perpendicular directions of the surface. Furthermore, the individual reflection elements have, in a first subregion, a convexly shaped application surface which faces toward a sample to be spectroscopically analyzed, in particular an aqueous or powdered sample. The application surface therefore forms the interface between a sample and a reflection element.

The convex shape of the application surface gives rise to several advantages. On the one hand, the convex shape allows the light beam to be guided by total internal reflection. On the other hand, owing to the convex shape of the application surface in combination with the regular arrangement as a matrix, an incompressible liquid, in particular water and/or blood, is displaced into channels formed by the convex shape during pressure on the sample. In this way, liquids which cause interference during the infrared spectroscopy, in particular water and/or blood, flow away through the channels which are formed. In this way, for example, the interfering effect of water absorption, which exists throughout the medium infrared wavelength range, particularly in the range from 4 µm to 10 µm, is significantly reduced. Aqueous and/or powdered samples can therefore advantageously be spectroscopically analyzed without great preparation outlay.

This is particularly advantageous for applications in surgery, in which tissue studies during an operation do not allow any preparation and the tissues are usually surrounded by complex liquids, in particular blood. Expediently, the water and/or blood on the tissue to be spectroscopically analyzed are displaced by the pressure of the convex application surface and removed from the measurement position by the channels which are formed. Advantageously, the arrangement of the reflection elements can moreover be adapted to the surface of an organ, for example a liver or kidney. Flush contact between the reflection matrix and the organ to be studied is thereby achieved. By the adaptation, the reflection elements are arranged regularly in a curved surface, which replicates the surface of an organ.

Advantageously, the reflection elements in a surface form a matrix. By the arrangement as a matrix, each reflection element can be assigned precisely one pixel during the ATR infrared spectroscopy, so that position resolution of the sample to be spectroscopically analyzed is furthermore made possible.

In the method, the following are carried out:
generation of an infrared light beam with an infrared light source,
entry of the light beam into a reflection element,
detection of the light beam reflected by the reflection element with at least one infrared detector.

The method allows illumination of at least one reflection element and detection of the light beam which exits from the reflection element, or is reflected thereby. An ATR infrared spectrum of a sample to be spectroscopically analyzed can therefore be obtained.

In an advantageous configuration, the reflection elements may be configured in the shape of a semicylinder in the first subregion. In this way, parallel channels are formed as a matrix in the arrangement. In this case, the channels extend for example along one of the mutually perpendicular directions.

Advantageously, total reflection of the light beam is made possible by the semicylindrical shape. It is particularly advantageous that incompressible liquids can flow away through the parallel channels. In particular, the incompressible liquids are displaced from the position of the total reflection and therefore from the measurement position.

In a particularly advantageous configuration, the reflection elements may be configured in the shape of a hemisphere in the first subregion. In this way, parallel channels are respectively formed as a matrix in the two mutually perpendicular directions of the matrix in the arrangement. In this way the number of channels is increased, so that the throughput of liquid is increased. It is particularly advantageous that the light beam can experience multiple total reflection because of the hemispherical configuration, so that the signal and therefore the signal-to-noise ratio can also be increased.

In a particularly advantageous configuration, the reflection elements may be configured in the shape of a pyramid in the first subregion. Advantageously, a pyramid has a rectangular base surface, which facilitates connection to a second subregion, which may be configured in the shape of a cuboid.

A second subregion of the reflection elements may be configured in the shape of a cuboid. The cuboid shape of the second subregion allows simple and accurately fitted, or flush, arrangement of the reflection elements as a matrix. It is advantageous that, because of the flush termination of the reflection elements, an incompressible liquid escapes through the channels and is not fed onto the surface of the second subregions which faces away from the sample.

In an advantageous configuration, the reflection elements of the reflection matrix may have a reflective coating, in particular for reflection of infrared radiation. The guiding of the light beam can be influenced in this way, so that a multiplicity of total reflections take place. In this way, the signal-to-noise ratio is increased. For example, circular guiding of the light beam is also possible. Instead of or in addition to a reflective coating, a multiplicity of materials having different refractive indices may also be used. By expedient matching of the refractive indices, it is possible to achieve desired guiding of the light beam, in particular by a multiplicity of total reflections of the light beam.

The reflection elements may be formed of at least one of the materials ZnSe, Ge, Si or diamond. Total internal reflection of the light beam is made possible by the high refractive index of the aforementioned materials. Ge, which has a refractive index of about 4, is particularly advantageous. In this way, a high resolution can be achieved in imaging methods.

In an advantageous refinement, a multiple reflection crystal allows multiple guiding of the same light beam to a reflection element. This gives rise to a multiplicity of repeated total reflections on the application surface of the reflection elements, so that the signal strength and therefore the signal-to-noise ratio are increased. Absorption bands which are characteristic in relation to the sample therefore become more pronounced.

The multiple reflection element may be arranged displaceably relative to the reflection matrix. In this way, it is possible to place the multiple reflection element over any desired reflection element of the reflection matrix. The placement may be carried out successively for each reflection element because of the displaceability, so that position resolution with a high signal-to-noise ratio is advantageously obtained.

In an advantageous refinement, the multiple reflection element and the second subregion of the reflection elements have an essentially equal refractive index. In this way, it is possible to avoid refraction of the light beam at the multiple reflection element/reflection element interface, which has a detrimental effect on the beam path.

According to an advantageous configuration, the light beam may be displaced along the reflection matrix, so that each individual reflection element is illuminated at least once. A scanning method is achieved by displacement of the light beam along the reflection matrix. Each reflection element of the reflection matrix is illuminated at least once, so that the method allows imaging of the sample. Advantageously, a pixel respectively corresponds to a measurement signal of a reflection element. It is therefore possible to record an ATR infrared spectrum for each pixel. It is particularly advantageous that imaging of the sample with a high signal strength is made possible by the method in combination with the reflection matrix. Particularly for applications in surgery, the method allows sufficient discrimination of tumor tissue from healthy, or normal, tissue.

In an advantageous configuration, the illumination of the individual reflection elements by the light from the light source may be carried out simultaneously in the method. In this way, an overall image of the sample is obtained. The position resolution is subsequently made possible in the detector by the use of a matrix detector (focal plane array). In this case, an ATR infrared spectrum is therefore recorded for each pixel.

In the method, the reflection elements can be pressed onto the sample to be spectroscopically analyzed. Advantageously, the signal strength is thereby increased. It is particularly advantageous that, by the application pressure of the reflection matrix, channels are formed which make it possible for incompressible liquids, in particular water and/or blood, to flow away. In this way, it is possible to avoid the interfering influence, in particular of water, on the measurement signal. Furthermore, advantageously, elaborate preparation of aqueous and/or powdered samples is not necessary. This is advantageous particularly for applications in surgery, in which tissue studies during an operation do not allow any preparation and the tissues are usually surrounded by liquids, in particular blood.

In an advantageous refinement, the light beam of the infrared light source enters first a multiple reflection element and then a reflection element. In this way, the light beam can advantageously be guided multiple times to the measurement position in the reflection element, so that the signal-to-noise ratio is increased.

It is advantageous for the light beam to enter a reflection element at least four times before the detection in the infrared detector. A number of entries equal to ten is particularly advantageous. This can be made possible by the multiple reflection element. The signal strength is approximately proportional to the number of total reflections at the reflection element/sample (application surface) interface. Multiple total reflection at the application surface can be achieved straightforwardly by the known multiple reflection elements.

BRIEF DESCRIPTION OF THE DRAWINGS

These and other aspects and advantages will become more apparent and more readily appreciated from the following description of the exemplary embodiments with reference to the accompanying drawings of which FIG. 3 is a three-dimensional representation of the reflection matrix with a multiple reflection element.

DETAILED DESCRIPTION OF THE PREFERRED EMBODIMENT

Figure 1:
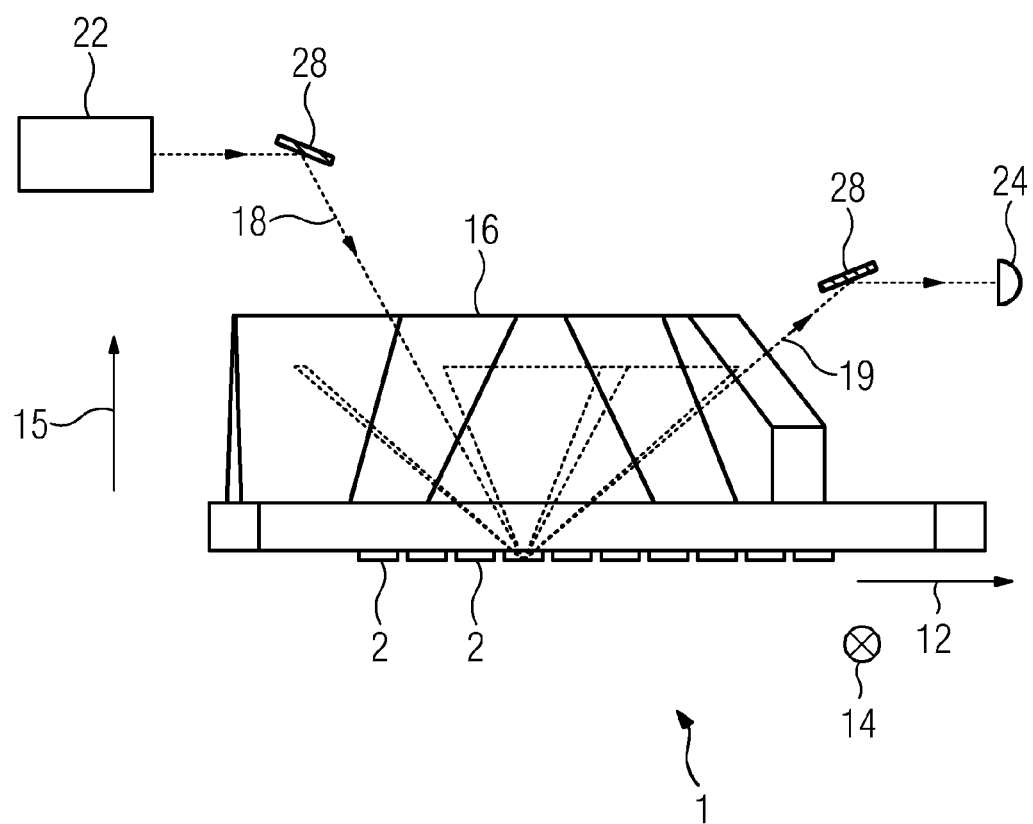
FIG. 1 is a side view of the arrangement for ATR infrared spectroscopy.

Reference will now be made in detail to the preferred embodiments, examples of which are illustrated in the accompanying drawings, wherein like reference numerals refer to like elements throughout.

FIG. 1 shows a cross section along a direction 12 of the reflection matrix 1, which is formed of individual reflection elements 2, with a multiple reflection crystal 16. The arrangement shown in this exemplary embodiment for ATR infrared spectroscopy furthermore includes an infrared light source 22, mirrors and/or general beam shaping components 28 and an infrared detector 24. An infrared light beam 18, coming from the infrared light source 22, first strikes the multiple reflection crystal 16. The multiple reflection crystal 16 guides the light beam 18 via a multiplicity of total internal reflections repeatedly to one of the reflection elements 2. The reflected light beam 19 subsequently emerges from the multiple reflection crystal 16 and is guided by mirrors and/or general beam shaping components 28 to the infrared detector 24 for detection. The multiple reflection crystal 16 is positioned in relation to a direction 15 above the reflection matrix 1 and is displaceable relative thereto in the mutually perpendicular directions 12, 14. Advantageously, an ATR infrared spectrum can thereby be recorded by the detector 24 for each reflection element 2 of the reflection matrix 1.

Because of the multiple guiding of the light beam 18 by the multiple reflection element 16, the signal strength is multiplied in this exemplary embodiment. As a result, imaging with a high signal-to-noise ratio is made possible.

Figure 2:
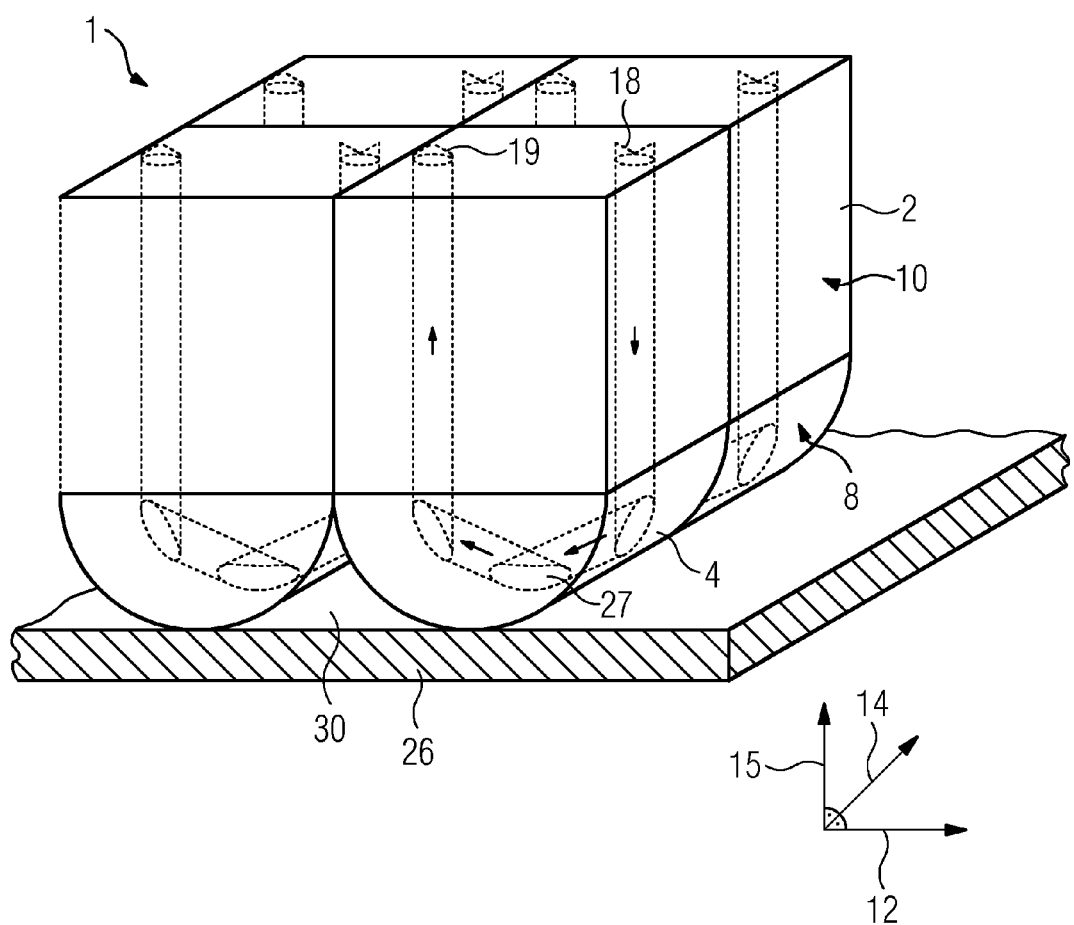
FIG. 2 is a three-dimensional representation of the reflection elements and their arrangement as a reflection matrix.

FIG. 2 shows a three-dimensional arrangement of the reflection elements 2. In this case, the reflection elements 2 are arranged regularly in the mutually perpendicular directions 12, 14 and form the reflection matrix 1. Typically, the extent of a reflection element 2 lies in the range of from about 0.5 mm to 1.5 mm. The light beam 18, which emerges from the infrared light source 22 (not shown here), enters at a right angle in relation to the two directions 12, 14 into a second subregion 10 of the reflection elements 2. The second subregion 10 is advantageously configured in the shape of a cuboid, so that a flush matrix arrangement of the reflection elements 2 is obtained. In this exemplary embodiment, the reflection elements 2 are configured with the shape of a semicylinder in the first subregion 8. The reflection elements could also be configured with the shape of a wedge. Advantageously, because of the convex shape of an application surface 4, channels 30 which make it possible for e.g. water and/or blood to flow away are formed. In this case, the water and/or blood in the vicinity of the sample 26 to be spectroscopically analyzed is displaced by the application pressure of the application surfaces 4 into the channels 30, and is transported away from the measurement position 27 by these. The light beam 19 emerging from the second subregion along the direction 15 may then be guided to the infrared detector 24 (not shown here) or returned again by the multiple reflection element 16 (not shown here) as a light beam 18 to the reflection element 2.

FIG. 3 shows a three-dimensional representation of the reflection matrix 1. The arrangement shown furthermore includes a multiple reflection crystal 16. The individual reflection elements 2 are arranged regularly in two mutually perpendicular directions 12, 14 in a flat plane 6. They therefore form the reflection matrix 1. In this case, the application surfaces 4 of the reflection elements 2 are located in front of the plane 6 in relation to the direction 15 perpendicular to the directions 12, 14, so that the application surfaces 4 can be pressed onto a sample 26 (not shown in this exemplary embodiment). As already explained with reference to FIG. 1, the light beam 18 first enters the multiple reflection element 16, then is guided multiply to the reflection elements 2, and subsequently emerges as the light beam 19.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. *DIRECTV,* 358 F3d 870, 69 USPQ2d 1865 (Fed. Cir. 2004).

The invention claimed is:

1. A system for infrared spectroscopy of a sample using attenuated total reflection, comprising:
    a light source producing a light beam;
    a reflection matrix having a multiplicity of reflection elements arranged on a matrix surface, the reflection elements being configured to guide the light beam by total internal reflection,
    a first subregion of each of the multiplicity of reflection elements having an application surface with a convex exterior shape, the application surface facing toward the sample to be spectroscopically analyzed,
    a second subregion of each of the multiplicity of reflection elements defining a transverse perimeter channeling the light beam into the first subregion of the respective reflection element and out of the first subregion and thereby out of the respective reflection element,
    the reflection elements being arranged in a matrix and disposed regularly in two mutually perpendicular directions of the matrix surface;
    a multiple reflection crystal configured to guide the light beam by total internal reflection multiple times to one of the reflection elements;
    beam shaping components directing the light beam at least one of to and from the multiple reflection crystal; and
    a detector detecting the light beam after reflection by the reflection matrix.

2. The system as claimed in claim 1, wherein the first subregion of the reflection elements comprises a semicylinder shape.

3. The system as claimed in claim 1, wherein the first subregion of each of the multiplicity of reflection elements has a convex shape of a hemisphere.

4. The system as claimed in claim 1, wherein the first subregion of each of the multiplicity of reflection elements has a convex shape of a pyramid.

5. The system as claimed in claim 1, wherein the second subregion of each of the multiplicity of reflection elements has a cuboid shape.

6. The system as claimed in claim 5, wherein the multiple reflection crystal and the second subregion of the reflection elements have substantially equal refractive indices.

7. The system as claimed in claim 1, wherein the reflection elements have a reflective coating.

8. The system as claimed in claim 1, wherein the reflection elements are constructed of at least one material selected from the group consisting of zinc selenium, germanium, silicon and diamond.

9. The system as claimed in claim 1, wherein the multiple reflection crystal is displaceable relative to the reflection matrix.

10. A method for infrared spectroscopy with a reflection matrix, comprising:
   generating an infrared light beam by an infrared light source;
   guiding the light beam by total internal reflection multiple times through a multiple reflection crystal to one of a plurality of reflection elements in the reflection matrix;
   wherein the light beam enters each of the plurality of reflection elements through a second subregion defining a transverse perimeter channeling the light beam into a first subregion of the respective reflection element;
   the first subregion of each of the plurality of reflection elements including an application surface with a convex exterior shape, the application surface facing toward the sample to be spectroscopically analyzed; and
   detecting the light beam after reflection in the first subregion by the respective reflection element by at least one infrared detector.

11. The method as claimed in claim 10, further comprising displacing the light beam along the reflection matrix until each of the reflection elements is illuminated at least once.

12. The method as claimed in claim 10, wherein said guiding of the light beam simultaneously illuminates a plurality of the reflection elements.

13. The method as claimed in claim 10, further comprising pressing application surfaces of the reflection elements onto a sample to be spectroscopically analyzed.

14. The method as claimed in claim 10, wherein said guiding of the light beam illuminates the one of the reflection elements at least four times before said detecting by the infrared detector.

* * * * *